(12) United States Patent
Mehta et al.

(10) Patent No.: US 7,220,407 B2
(45) Date of Patent: May 22, 2007

(54) G-CSF THERAPY AS AN ADJUNCT TO REPERFUSION THERAPY IN THE TREATMENT OF ACUTE MYOCARDIAL INFARCTION

(75) Inventors: Jayesh Mehta, Chicago, IL (US); Seema Singhal, Chicago, IL (US); Charles Davidson, Winnetka, IL (US); Nirat Beohar, Chicago, IL (US); Robert Bonow, Glencoe, IL (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 10/694,579

(22) Filed: Oct. 27, 2003

(65) Prior Publication Data

US 2005/0089507 A1    Apr. 28, 2005

(51) Int. Cl.
A61K 38/19    (2006.01)
A61K 38/20    (2006.01)
A61K 38/18    (2006.01)
A61K 45/00    (2006.01)

(52) U.S. Cl. .................. 424/85.1; 424/85.2; 435/1.2; 514/12

(58) Field of Classification Search .................. 514/2
See application file for complete search history.

(56) References Cited

U.S. PATENT DOCUMENTS

| 4,810,643 | A | 3/1989 | Souza |
| 4,904,584 | A | 2/1990 | Shaw |
| 5,104,651 | A | 4/1992 | Boone et al. |
| 5,214,132 | A | 5/1993 | Kuga et al. |
| 5,218,092 | A | 6/1993 | Sasaki et al. |
| 5,362,853 | A | 11/1994 | Kuga et al. |
| 5,606,024 | A | 2/1997 | Boone et al. |
| 5,824,778 | A | 10/1998 | Ishikawa et al. |
| 5,824,784 | A | 10/1998 | Kinstler et al. |
| 6,017,876 | A | 1/2000 | Gegg et al. |
| 6,166,183 | A | 12/2000 | Ishikawa et al. |
| 6,261,550 | B1 | 7/2001 | Osslund |
| 2002/0061587 | A1* | 5/2002 | Anversa .................. 435/366 |
| 2003/0064922 | A1 | 4/2003 | Nissen et al. |

FOREIGN PATENT DOCUMENTS

| AU | A-76380/91 | 11/1991 |
| AU | A-10948/92 | 8/1992 |
| EP | 0 243153 | 10/1987 |
| EP | 0 256843 | 2/1988 |
| EP | 0 272703 | 6/1988 |
| EP | 0 335423 | 10/1989 |
| EP | 0 370205 | 5/1990 |
| EP | 0 401384 | 12/1990 |
| EP | 0 456200 | 11/1991 |
| EP | 0 459630 | 12/1991 |
| EP | 0 473268 | 3/1992 |
| EP | 1129720 | 9/2001 |
| EP | 1327449 | 7/2003 |
| WO | WO 88/00969 | 2/1988 |
| WO | WO 89/05824 | 6/1989 |
| WO | WO 89/10932 | 11/1989 |
| WO | WO 90/06952 | 6/1990 |
| WO | WO 90/12874 | 11/1990 |
| WO | WO 91/05798 | 5/1991 |
| WO | WO 91/11520 | 8/1991 |
| WO | WO 91/18911 | 12/1991 |
| WO | WO 92/04455 | 3/1992 |
| WO | WO 92/06116 | 4/1992 |
| WO | WO 92/06707 | 4/1992 |
| WO | WO 93/05169 | 3/1993 |
| WO | WO 93/15211 | 8/1993 |
| WO | WO 94/20069 | 9/1994 |
| WO | WO 95/21629 | 8/1995 |
| WO | WO 96/11953 | 4/1996 |
| WO | WO 01/51510 | 7/2001 |
| WO | WO 03/006501 | 1/2003 |
| WO | WO 03/030821 | 4/2003 |

OTHER PUBLICATIONS

Vallely et al., The J of Thoracic and Cardiovascular Surgery, vol. 124(4): pp. 758-767, esp. p. 761, Figure 1.*

Hiltunen, et al. Nerve growth factor and brain-derived neurotrophic factor mRNAs are regulated in distinct cell populations of rat heart after ischaemia and reperfusion. J Pathol. Jun. 2001;194(2):247-53.*

Gottlieb et al., Apoptosis in myocardial ischemia-reperfusion. Ann N Y Acad Sci. Jun. 30, 1999;874:412-26. Review.*

Melillo et al., Intrinsic Myocyte Dysfunction and Tryrosine Kinase Pathway Activation Underlie the Imparied Wall Thickening of Adjacent Regions During Postinfarct Left Venricular Remodeling. 1996 Circulation 93:1447-58.*

Stedman's Medical Dictionary 27th Edition, 2000 Lippincott Williams & Wilkins.*

Kukielka et al., Interleukin-8 Gene Induction in the Myocardium after Ischemia and Reperfusion in Vivo. J Clin Invest. Jan. 1995 95:89-103.*

Colquhoun et al., Reversal of neutropenia with granulocyte colony-stimulating factor without precipitating liver allograft rejection, *Transplantation* 56:755-758, 1993.

(Continued)

*Primary Examiner*—Janet L. Andres
*Assistant Examiner*—Cherie Woodward
(74) *Attorney, Agent, or Firm*—Marshall, Gerstein & Borun LLP

(57) ABSTRACT

The present invention relates to methods of using Granulocyte Colony Stimulating Factor (G-CSF) polypeptide in conjunction with reperfusion therapy in the treatment of acute myocardial infarction or other ischemic events. This treatment can be used alone or in combination with other well-known methods of treatment.

14 Claims, No Drawings

OTHER PUBLICATIONS

Diflo et al., Simultaneous use of ganciclovir and granulocyte colony stimulating factor in liver transplant recipients, *Hepatology* 16:PA278A, 1992.

Ferrari, et al., Muscle regeneration by bone marrow-derived myogenic progenitors, *Science* 279:1528-1530, 1998.

Fukunaga et al., Growth and differentiation signals mediated by different regions in the cytoplasmic domain of granulocyte colony-stimulating factor receptor, *Cell* 74:1079-1087, 1993.

Gabrilove, Introduction and overview of hematopoietic growth factors, *Semin. Hematol.* 26:2 (Suppl 2):1-4, 1989.

Görgen et al., Granulocyte colony-stimulating factor treatment protects rodents against lipopolysaccharide-induced toxicity via suppression of systemic tumor necrosis factor-α, *J. Immunol.* 149:918-924, 1992.

Jones et al., Growth factors in haemopoiesis, *Bailliere's Clin. Hematol.* 2:83-111, 1989.

Kocher et al., Neovascularization of ischemic myocardium by human bone-marrow-derived angioblasts prevents cardiomyocyte apoptosis, reduces remodeling and improves cardiac function, *Nature Med.* 7:430-436, 2001.

Kuga et al., Mutagenesis of human granulocyte colony stimulating factor, *Biochem. Biophys. Res. Comm.* 159:103-111, 1989.

Lachaux et al., Treatment with lenograstim (glycosylated recombinant human granulocyte colony-stimulating factor) and orthotopic liver transplantation for glycogen storage disease type Ib, *J. Ped.* 123:1005-1008, 1993.

Lange et al., Reperfusion therapy in acute myocardial infarction, *N. Engl. J. Med.* 346:954-955, 2002.

Lu et al., Disulfide and secondary structures of recombinant human granulocyte colony stimulating factor, *Arch. Biochem. Biophys.* 268:81-92, 1989.

Moore et al., Synergy of interleukin 1 and granulocyte colony-stimulating factor: In vivo stimulation of stem-cell recovery and hematopoietic regeneration following 5-fluorouracil treatment of mice, *Proc. Natl. Acad. Aci. USA* 84:7134-7138, 1987.

Orlic et al., Bone marrow cells regenerate infarcted myocardium, *Nature (London)* 410:701-705, 2001.

Orlic et al., Mobilized bone marrow cells repair the infarcted heart, improving function and survival, *Proc. Nat. Acad. Sci USA* 98:10344-10347, 2001.

Orlic et al., Adult bone marrow stem cells regenerate myocardium in ischemic heart disease, *Ann. N.Y. Acad. Sci.* 996: 152-157, 2003.

Rosenthal et al., Bone marrow-derived angioblasts may be used to promote cardiac revascularization in the days following a myocardial infarction, *Nature Medicine* 7:412-413, 2001.

Souza et al., Recombinant human granulocyte colony-stimulating factor: Effects on normal and leukemic myeloid cells, *Science* 232:61-65, 1986.

Takano et al., Pleiotropic effects of cytokines on acute myocardial infarction: G-CSF as a novel therapy for acute myocardial infarction, *Curr. Pharm. Des.* 9.1121-1127, 2003.

Welte et al., Purification and biochemical characterization of human pluripotent hematopoietic colony-stimulating factor, *Proc. Natl. Acad. Sci. USA* 82: 1526-1530, 1985.

Wright et al., Granulocyte colony-stimulating factor (GCSF) combined with αinterferon (αIFN) for treatment of liver allograft recipients with viral hepatitis, *Hepatology* 14:PA48, 1991.

Ambler et al., "Integration of bone marrow-derived stem cells into infracted myocardium following ischemia-reperfusion in mice," Abstract No. 413.7, *FASEB Journal* 17:4-5, 2003.

Engelmann et al., "Placebo-controlled, randomized, double-blind study on the efficacy of bone-marrow stem cell mobilization induced by granulocyte-colony stimulating factor (G-CSF) on improvement of ischemic heart failure undergoing delayed revascularization for ST segment elevation myocardial infarction (STEM)," Abstract No. 2829, *Circulation* 108 (17) Suppl.:IV-622, 2003.

Goltermann, "Reperfusion of acute coronary syndromes and myocardial infarction," *Air Medical Journal* 19:47-49, 2000.

Hellström-Lindberg et al., "Treatment of anemia in myelodysplastic syndromes with granulocyte colony-stimulating factor plus erythropoietin: Results from a randomized phase II study and long-term follow-up of 71 patients," *Blood* 92:68-75, 1998.

Kuramochi et al., "Granulocyte-colony stimulating factor (G-CSF) administeration improves cardiac function after myocardial infarction in mice without altering cardiomyocyte regeneration," Abstract No. 99, *Circulation*, 106:19 (Suppl.): 11-20, 2002.

Li et al., "Efficiency of granulocyte colony stimulating factor (G-CSF) on cardiac function and cytokines in rat model acute myocardial infarction," Abstract No. 3P-0648, *Artherosclerosis Supplements*, 4 (2):204, 2003.

Mehta et al., "Early administration of a filgrastim following experimental myocardial infarction in a porcine ischemia reperfusion model may help myocardial repair," Abstract No. 4328, *Blood* 102:154b-155b, 2003.

Minatoguchi et al., "Acceleration of the healing process and myocardial regeneration may be important as a mechanism of improvement of cardiac function and remodeling by postinfarction granulocyte colony-stimulating factor treatment," *Circulation*, 109:2572-2580, 2004.

Minatoguchi et al., "Myocardial infarction itself induces cardiomyocyte regeneration from bone marrow cells, and post-ischemic G-CSF treatment improves cardiac dysfunction via acceleration of the process," Abstract No. 666, *Circulation* 106 (19) Suppl.:II-132-133, 2002.

Schwartz et al., "Autologous stem cells for functional myocardial repair," *Heart Failure Reviews*, 8:237-245, 2003.

* cited by examiner

G-CSF THERAPY AS AN ADJUNCT TO REPERFUSION THERAPY IN THE TREATMENT OF ACUTE MYOCARDIAL INFARCTION

FIELD OF THE INVENTION

The present invention relates to the use of Granulocyte Colony Stimulating Factor (G-CSF) polypeptide in the prevention or treatment of injury to the myocardium after acute myocardial infarction (AMI) or other ischemic events. More particularly, the invention provides methods of treating AMI by the administration of G-CSF polypeptide in conjunction with reperfusion therapy.

BACKGROUND OF THE INVENTION

Acute myocardial infarction (AMI) refers to a blockage of one or more of the coronary arteries. Coronary arterial occlusion due to thrombosis is the cause of most cases of AMI. This blockage restricts the blood supply to the muscle walls of the heart and is often accompanied by symptoms such as chest pain, heavy pressure in the chest, nausea, and shortness of breath, or shooting pain in the left arm. AMI is accompanied with an inflammatory reaction which induces cardiac dysfunction and scarring. Rapid restoration of blood flow to jeopardized myocardium limits necrosis and reduces mortality. There are approximately 1.5 million cases of AMI in the United States each year, resulting in more than 500,000 deaths. Many of the deaths resulting from AMI occur before the patient can reach the hospital.

Over the last two decades, AMI mortality has been reduced through therapeutic developments and advances in cardiovascular intervention. Reperfusion therapy for the treatment of AMI consists of primary angioplasty and/or administration of a thrombolytic agent. This can be accomplished mechanically, with primary balloon angioplasty or stenting, or medically, with a thrombolytic agent. Each method has its advantages and limitations (*N. Engl. J Med.* 346:954–955, 2002). The choice of reperfusion therapy in the individual patient will depend on the facilities available, contraindications for an individual patient, and the cost. The aim should be the earliest possible successful reperfusion with the least risk of complications and in the most cost-effective manner. The critical time is the time to reperfusion.

In primary angioplasty, a catheter affixed with an inflatable balloon is inserted into the patient's artery and guided to the site of the blockage where the balloon is inflated to effectively force open the clot and restore blood flow to the heart walls before permanent damage occurs. In thrombolytic therapy, clot-busting drugs or thrombolytics are administered soon after a heart attack. Commonly used thrombolytics include streptokinase and tissue plasminogen activators. Blood thinners, like heparin and aspirin, are also effective for some patients.

AMI leads to rapid death of myocytes and vascular structures in the supplied region of the ventricle. The loss of myocytes, arterioles, and capillaries in the infarcted area is irreversible, resulting with time in the formation of scarred tissue. Recent reports have demonstrated that implanted bone marrow cells (BMC) could differentiate into myocytes and coronary vessels ameliorating the function of the injured heart (Orlic et al., *Nature* (London) 410: 701–705, 2001). These same researchers showed that the mobilization of primitive BMC prior to AMI, by the administration of granulocyte colony stimulating factor (G-CSF) in combination with stem cell factor (SCF) resulted in a significant degree of tissue regeneration in the ischemic site (Orlic et al. *Proc. Nat. Acad. Sci.* 98:10344–10347, 2001). Their findings in a mouse model of AMI, induced by coronary artery ligation, suggested that the mobilization of primitive BMC by cytokines might offer a noninvasive therapeutic strategy for the regeneration of the myocardium lost as a result of AMI or other pathology.

Currently available treatments for AMI, such as thrombolytic therapy and percutaneous coronary interventions, require a hospital setting including the availability of a cardiac catheterization laboratory so that there is an inherent time lag between onset of AMI and the administration of therapy. Thus, there is a need to develop quick, easy, and effective treatments for AMI to reduce the damage to the heart after a coronary occlusion. Accordingly, an object of the present invention is to provide such methods for the treatment of AMI, which are discussed in further detail herein.

SUMMARY OF THE INVENTION

The present invention relates the use of Granulocyte Colony Stimulating Factor (G-CSF) polypeptides in the treatment of acute myocardial infarction (AMI) and myocardial ischemia. More specifically, the invention provides methods useful in conjunction with reperfusion therapy for minimizing tissue damage and improving patient outcome after such myocardial injury, illustratively through prevention of cardiac wall thickness loss ordinarily attending ischemia in affected tissues.

In one aspect, therefore, the present invention provides methods of treating AMI to reduce heart damage. Such a method generally would comprise administering an effective amount of a composition comprising a G-CSF polypeptide to mammals, including humans, commencing before, concurrently with, and/or after reperfusion therapy.

The term "G-CSF polypeptide" or "G-CSF" as used herein is defined as naturally occurring human and heterologous species G-CSF, recombinantly produced G-CSF that is the expression product consisting of either 174 or 177 amino acids, or fragments, analogs, variants, or derivatives thereof as reported, for example in Kuga et al., Biochem. Biophys. Res. Comm. 159: 103–111 (1989); Lu et al., Arch. Biochem. Biophys. 268: 81–92 (1989); U.S. Pat. Nos. 4,810,643, 4,904,584, 5,104,651, 5,214,132, 5,218,092, 5,362,853, 5,606,024, 5,824,778, 5,824,784, 6,017,876, 6,166,183, and 6,261,550; U.S. patent application No. US 2003/0064922; EP 0 335423; EP 0 272703; EP 0 459630; EP 0 256843; EP 0 243153; WO 9102874; Australian Application document Nos. AU-A-10948/92 and AU-A-76380/91. Included are chemically modified G-CSFs, see, e.g., those reported in WO 9012874, EP 0 401384 and EP 0 335423. See also, WO 03006501; WO 03030821; WO 0151510; WO 9611953; WO 9521629; WO 9420069; WO 9315211; WO 9305169; JP 04164098; WO 9206116; WO 9204455; EP 0 473268; EP 0 456200; WO 9111520; WO 9105798; WO 9006952; WO 8910932; WO 8905824; WO 9118911; and EP 0 370205. Also encompassed herein are all forms of G-CSF, such as ALBUGRANIN™, NEUULASTA™, NEUPOGEN®, and GRANOCYTE®.

In another aspect, the invention provides methods of treating an ischemic injury. Such a method generally would comprise administering an effective amount of a composition comprising G-CSF polypeptide to a mammal, commencing before, concurrently with, or after reperfusion therapy.

The reperfusion therapy contemplated includes mechanical (primary angioplasty), chemical (administration of a thrombolytic agent), and surgical (coronary bypass surgery) means.

The term "thrombolytic agent" is meant to refer to any agent capable of either dissolving a fibrin-platelet clot, or inhibiting the formation of such a clot. Examples of thrombolytic agents include streptokinase, prourokinase, urokinase, and tissue-type plasminogen activator. Although natural t-PA may be employed, it is preferable to employ recombinant t-PA. The invention may additionally employ hybrids, physiologically active fragments or mutant forms of the above thrombolytic agents. The term "tissue-type plasminogen activator" as used herein is intended to include such hybrids, fragments and mutants, as well as both naturally derived and recombinantly derived tissue-type plasminogen activator.

The invention further provides a method, wherein the thrombolytic or fibrinolytic agent is selected from the group consisting of streptokinase, urokinase, prourokinase, and tissue-type plasminogen activator. Additional tissue-type plasminogen activator variants such as alteplase, reteplase, and anistreplase are also contemplated.

In a further embodiment, the invention provides a method, wherein the composition includes the use of at least one additional factor. The additional factor, is selected from the group consisting of: EPO, SCF, M-GDF, GM-CSF, M-CSF, CSF-1, IL-1, IL-2, IL-3, IL-4, IL-5, IL-6, IL-7, IL-8, IL-9, IL-10, IL-11, IL-12, interleukins, IGF-1, LIF, interferon, a neurotrophic factor, a fibroblast growth factor, and human growth hormone. Furthermore, the invention provides a method wherein the effective amount of the G-CSF polypeptide is about 0.001 μg/kg body weight/day to about 1000 μg/kg body weight/day. A preferred amount is 300 μg per day.

The invention further comprehends kits containing components for treating myocardial infarction and ischemia, as set out above. Such a kit generally would comprise a composition comprising G-CSF polypeptide; and optionally, at least one additional factor selected from the group consisting of: a thrombolytic agent, EPO, SCF, M-GDF, GM-CSF, M-CSF, CSF-1, IL-1, IL-2, IL-3, IL-4, IL-5, IL-6, IL-7, IL-8, IL-9, IL-10, IL-11, IL-12, interleukins, IGF-1, LIF, interferon, a neurotrophic factor, a fibroblast growth factor, and human growth hormone.

DETAILED DESCRIPTION OF THE INVENTION

G-CSF has been found to be useful alone, or in combination with stem cell factor (SCF) in the mobilization of bone marrow stem cells. Studies have also indicated that implanted bone marrow cells (BMC) could differentiate into myocytes and coronary vessels to improve function in an the injured heart (Orlic et al., *Nature* (London) 410: 701–705, 2001). The mobilization of primitive BMC prior to AMI, by the administration of G-CSF along with stem cell factor (SCF), also resulted in a significant degree of tissue regeneration in the ischemic site (Orlic et al. *Proc. Nat. Acad. Sci* 98:10344–10347, 2001). These studies suggested that the mobilization of primitive BMC by cytokines to the injured heart might offer a noninvasive therapeutic strategy for the regeneration of injured myocardium resulting from AMI or other pathology.

The present invention addresses a role for G-CSF polypeptide in the treatment of AMI and myocardial ischemia. More specifically, the invention contemplates methods for minimizing tissue damage and improving patient outcome after such myocardial injury.

According to the invention, treatment with an effective amount of G-CSF polypeptide in an animal model of human AMI, administered immediately after reperfusion therapy, reduced heart damage. More specifically, the treatment increased ventricular wall thickness. These findings provide the first evidence of a method of treating AMI and myocardial ischemia with G-CSF polypeptide in conjunction with reperfusion therapy.

Discussed in further detail herein below are the roles of G-CSF in the mobilization of stem cells, the role of bone marrow stem cells in tissue repair and regeneration, and the events which take place in myocardial infarction and reperfusion therapy. Also described are methods of using G-CSF polypeptide in conjunction with reperfusion therapy for the treatment of AMI.

The section headings are used herein for organizational purposes only, and are not to be construed as in any way limiting the subject matter described.

A. Roles of G-CSF in the Mobilization of Stem Cells and Other Conditions

In one embodiment, the methods of the present invention exploit the use of G-CSF polypeptide in the mobilization of stem cells to the myocardium to minimize damage or increase repair in the AMI infarct zone. G-CSF causes an increase in the release of hematopoietic stem cells into the blood, and plays a role in the proliferation, differentiation, and survival of myeloid progenitor cells (Takano et al., Curr. Pharm. Des. 9:1121–1127, 2003). G-CSF and other hematopoietic growth factors including interleukin-3 (IL-3), IL-6, granulocyte-macrophage colony stimulating factors (GM-CSF), and stem cell factor (SCF) have all been reported to be positive regulators of granulopoiesis, the production of granulocytes in the bone marrow (Takano et al., Curr. Pharm. Des. 9:1121–1127, 2003).

Some research reports have indicated that G-CSF mobilized bone marrow stems cells can promote myocardial repair. For example, Kocher et al. (Nature Med. 7:430–436, 2001) demonstrated that the intravenous injection of adult human bone-marrow-derived endothelial cell precursors, mobilized by treatment with G-CSF, into a rat model of myocardial ischemia induced neoangiogenesis in the infarcted zone; prevented cardiomyocyte apoptosis; reduced scar formation, and improved ventricular function.

G-CSF also has been shown to specifically stimulate the proliferation and differentiation of neutrophilic precursor cells into mature neutrophils (Fukunaga et al., Cell 74:1079–1087, 1993), and is well known for its usefulness in the treatment of neutropenic states (Welte et al., Proc. Natl. Acad. Sci. USA 82:1526–1530, 1985; Souza et al., Science 232:61–65, 1986; Gabrilove, Sem. Hematol. 26:1–14, 1989). G-CSF increases the number of circulating granulocytes and has been reported to ameliorate infection in sepsis models. G-CSF administration also inhibits the release of tumor necrosis factor (TNF), a cytokine important to tissue injury during sepsis and rejection (Wendel et al., J. Immunol. 149:918–924, 1992).

Accordingly, G-CSF has been found to be useful in the treatment of conditions where an increase in neutrophils will provide benefits. For example, for cancer patients, G-CSF is beneficial as a means of selectively stimulating neutrophil production to compensate for hematopoietic deficits resulting from chemotherapy or radiation therapy. Other indications include treatment of various infectious diseases and related conditions, such as sepsis, which is typically caused by a metabolite of bacteria. G-CSF is also useful alone, or in combination with other compounds, such as other cytokines, for growth or expansion of cells in culture (for example, for bone marrow transplants or ex vivo expansion). G-CSF has been administered to transplant patients as an adjunct to treatment of infection or for treatment of neutropenia [Diflo et al., Hepatology 16:PA278 (1992); Wright et al., Hepatology 14:PA48 (1991); Lachaux et al., J. Ped. 123:1005–1008 (1993); Colquehoun et al., Transplantation 56:755–758 (1993)].

G-CSF is produced by fibroblasts, macrophages, T cells, trophoblasts, endothelial cells, and epithelial cells, and is the expression product of a single copy gene comprised of four exons and five introns located on chromosome seventeen. In humans, endogenous G-CSF is detectable in blood plasma (Jones et al., Bailliere's Clin. Hematol. 2:83–111, 1989). G-CSF is species cross-reactive, such that when human G-CSF is administered to another mammal such as a mouse, canine, or monkey, sustained neutrophil leukocytosis is elicited (Moore et al., Proc. Natl. Acad. Sci. USA 84:7134–7138, 1987).

Human G-CSF can be obtained and purified from a number of sources Natural human G-CSF can be isolated from the supernatants of cultured human tumor cell lines. The development of recombinant DNA technology has enabled the production of commercial scale quantities of G-CSF in glycosylated form as a product of eukaryotic host cell expression, and of G-CSF in non-glycosylated form as a product of prokaryotic host cell expression. See, for example, U.S. Pat. No. 4,810,643 (Souza) incorporated herein by reference.

B. Bone Marrow Stem Cells and Tissue Regeneration

The present invention contemplates methods of using G-CSF polypeptide in conjunction with reperfusion therapy protocols to stimulate the mobilization of bone marrow stem cells in the treatment of AMI. The present section provides a brief summary of what is known about the role of bone marrow stem cells in tissue regeneration to the extent that such a summary will facilitate a better understanding of the methods of the present invention.

Primitive cells in bone marrow have the capacity, both in vitro and in vivo, to give rise to cells of all three germ layers. Stem cells of mesenchymal/stromal and hematopoietic origin have been suggested to have the potential to differentiate like embryonic stem cells. However, the mechanism for this "transdifferentiation" of adult stem cells is controversial and not well understood (Orlic et al., Ann. N.Y. Acad. Sci. 996: 152–157, 2003).

Bone marrow stem cell regeneration has been demonstrated in a variety of tissues including, but not only, muscle (Ferrari et al., Science 279:1528–1530, 1998) and heart (Jackson et al., J. Clin. Invest. 107:1395–1402; Kocher et al., Nature Med. 7: 430–436, 2001; Orlic et al., Nature 410: 701–705, 2001; and Orlic et al., Proc. Natl. Acad. Sci. USA 98:10344–10349, 2001). Orlic et al. (Nature 410: 701–705, 2001) used direct injection of bone marrow stem cells into the heart three to five hours after ligation of the left coronary artery in a mouse model, resulting in the generation of new cardiomyocytes and endothelial cells in the zone of ischemic myocardium. These same researchers later reported that the proliferation of bone marrow stem cells in mice, effected by the treatment of mice with G-CSF prior to affecting occlusion of the left coronary artery, could ameliorate myocardial injury induced by the occlusion (Orlic et al., Proc. Natl. Acad. Sci. USA 98:10344–10349, 2001). Taken together, these studies suggest that stem cell therapy provides a novel therapeutic strategy in regenerating myocardium and treating heart disease.

C. Myocardial Infarction and Reperfusion Therapy

As discussed throughout the specification, the present invention contemplates methods of using G-CSF polypeptide in conjunction with reperfusion therapy protocols for the treatment of AMI. The present section provides an overview of the events which take place in myocardial infarction and reperfusion to the extent that such a description will facilitate a better understanding of the methods of the present invention.

Occlusion of the left coronary artery due to thrombosis is the major cause of AMI accompanied by ST-segment elevation. The loss of blood flow to the tissue from the inclusion causes damaged myocardium due to ischemia, infarction, necrosis, and scar formation. The expedient restoration of blood flow to the jeopardized area minimizes tissue damage and improves patient outcome. This restoration of blood flow, "reperfusion," can be accomplished medically, with a thrombolytic agent, or mechanically, with balloon angioplasty or stenting (Lange et al., N. Engl. J. Med. 346: 954–955, 2002).

Although reperfusion therapy provides relief to the damaged tissue and inhibits further scarring of the myocardium, the infarcted myocardium does not regenerate. Thus, AMI is a critical event which can lead to progressive heart failure and even death. Therefore, the present invention provides a novel method of using G-CSF polypeptide in conjunction with reperfusion therapy to minimize myocardial damage after AMI.

D. Methods of Using G-CSF

As mentioned herein above, it is contemplated that methods of the present invention will use G-CSF polypeptide in conjunction with reperfusion therapy in the treatment of AMI. G-CSF has been found to be useful in the treatment of conditions, where the mobilization of stem cells will provide benefits. G-CSF is useful alone, or in combination with other compounds, which may act as thromobolytic agents or expedite tissue repair. The present section provides a description of how G-CSF may be therapeutically administered in the methods of the invention.

a. Protein-Based Therapy

One of the therapeutic embodiments of the present invention is the provision, to a subject in need thereof, compositions comprising G-CSF polypeptide. G-CSF polypeptide may have been generated through recombinant means or by automated peptide synthesis. The G-CSF formulations for such a therapy may be selected based on the route of administration and may include liposome and micelle formulations as well as classic pharmaceutical preparations.

The G-CSF proteins are formulated into appropriate preparation and administered to one or more sites within the subject in a therapeutically effective amount. In particularly preferred embodiments, the human G-CSF protein-based therapy is effected via continuous or intermittent intravenous administration. By "effective amount" the present invention refers to that amount of human G-CSF polypeptide that is sufficient to support an observable change in the level of one or more biological activities of G-CSF. The change may be an increased level of G-CSF activity. Preferably, the change is an increase in bone marrow stem cell mobilization or circulation to the ischemic or damaged tissue resulting in diminished tissue damage or increased tissue growth.

Those of skill in the art will understand that the amounts of human G-CSF polypeptides administered for therapeutic use may vary. It is contemplated that the specific activity of the human G-CSF protein preparation may be in the range of about 100 units/mg of protein to about 500 units/mg protein. Thus, a given preparation of a human G-CSF protein may comprise about 100 units/mg protein, about 125 units/mg protein, about 150 units/mg protein, about 175 units/mg protein, about 200 units/mg protein, about 225 units/mg protein, about 250 units/mg protein, about 275 units/mg protein, about 300 units/mg protein, about 325 units/mg protein, about 350 units/mg protein, about 375 units/mg protein, about 400 units/mg protein, about 425 units/mg protein, about 450 units/mg protein, about 475 units/mg protein and about 500 units/mg protein. A particularly preferred range is from about 100 units/mg protein to about 200 units/mg protein; a more preferable range is between about 150 to about 200 units/mg protein. Preferably, the protein composition is substantially free of contaminating factors, contamination level of less than 0.02% (w/w). Human G-CSF compositions, suitable for injection into a patient, can be prepared, for example, by reconstitution with a pharmacologically acceptable diluent of a lyophilized sample comprising purified human G-CSF and stabilizing salts.

Administration of the compositions can be systemic or local, and may comprise a single site injection of a therapeutically-effective amount of the human G-CSF protein composition. Any route known to those of skill in the art for the administration of a therapeutic composition of the invention is contemplated including, for example, intravenous, intramuscular, subcutaneous or a catheter for long-term administration. Alternatively, it is contemplated that the therapeutic composition may be delivered to the patient at multiple sites. The multiple administrations may be rendered simultaneously or may be administered over a period of several hours. In certain cases, it may be beneficial to provide a continuous flow of the therapeutic composition. Additional therapy may be administered on a period basis, for example, daily, weekly, or monthly.

b. Combination Therapy

In addition to therapies based solely on the delivery of the human G-CSF, combination therapy is specifically contemplated. In the context of the present invention, it is contemplated that the human G-CSF therapy could be used similarly in conjunction with other agents commonly used for the treatment of AMI in conjunction with reperfusion.

To achieve the appropriate therapeutic outcome, using the methods and compositions of the present invention, one would generally provide a composition comprising human G-CSF and at least one other therapeutic agent (second therapeutic agent). In the present invention, it is contemplated that the second therapeutic agent may involve the administration or inclusion of at least one additional factor selected from the group consisting of: EPO, M-GDF, SCF, GM-CSF, M-CSF, CSF-1, IL-1, IL-2, IL-3, IL-4, IL-5, IL-6, IL-7, IL-8, IL-9, IL-10, IL-11, IL-12, or other various interleukins, IGF-1, LIF, interferon (such as a, β, gamma or consensus), neurotrophic factors (such as BDNF, NT-3, CTNF or noggin), other multi-potent growth factors (such as, to the extent these are demonstrated to be such multi-potent growth factors, flt-3/flk-2 ligand, stem cell proliferation factor, and totipotent stem cell factor), fibroblast growth factors (such as FGF), human growth hormone and analogs, fusion molecules, and other derivatives of the above. For example, G-CSF in combination with SCF has been found to mobilize peripheral blood progenitor cells in vivo. Ex vivo, for example, G-CSF in combination with SCF, IL-3 and IL-6 has been found useful for expansion of peripheral blood cells. Likewise, G-CSF will provide for similar uses.

The combination therapy compositions would be provided in a combined amount effective to produce the desired therapeutic outcome in the treatment of AMI in conjunction with reperfusion. This process may involve contacting the cells with human G-CSF polypeptide and the second agent(s) or factor(s) at the same time. This may be achieved by administering a single composition or pharmacological formulation that includes both agents, or by administering two distinct compositions or formulations, at the same time, wherein one composition includes the human G-CSF therapeutic composition and the other includes the second therapeutic agent.

Alternatively, the human G-CSF treatment may precede or follow the other agent treatment by intervals ranging from minutes to weeks. In embodiments where the second therapeutic agent and the human G-CSF are administered separately, one would generally ensure that a significant period of time did not expire between the times of each delivery, such that the second agent and the human G-CSF would still be able to exert an advantageously combined effect. In such instances, it is contemplated that one would administer both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Systemic delivery of human G-CSF expression constructs or proteins to patients may be a very efficient method for delivering a therapeutically effective gene to counteract the immediate clinical manifestations of a disease. Alternatively, local delivery of the human G-CSF and/or the second therapeutic agent may be appropriate in certain circumstances.

E. Pharmaceutical Compositions

As mentioned herein above, the present invention also comprehends methods using pharmaceutical compositions comprising effective amounts of G-CSF polypeptide together with pharmaceutically acceptable diluents, preservatives, solubilizers, emulsifiers, adjuvants and/or carriers useful in G-CSF therapy. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., thimersol, benzyl alcohol), and bulking substances (e.g., lactose, mannitol); incorporation of the material into particulate preparations of polymeric compounds, such as polylactic acid, polyglycolic acid, etc., or in association with liposomes or micelles. Such compositions will influence the physical state, stability, rate of in vivo release, and rate of in vivo clearance of the G-CSF. See, e.g., Remington's Pharmaceutical Sciences, 18th Ed. (1990) Mack Publishing Co., Easton, Pa., pages 1435–1712, which are herein incorporated by reference.

Derivatives of G-CSF are also comprehended herein. Such derivatives include molecules modified by one or more water soluble polymer molecules, such as polyethylene glycol, or by the addition of polyamino acids, including fusion proteins (procedures for which are well-known in the art). Such derivatization may occur singularly at the N- or C-terminus or there may be-multiple sites of derivatization. Substitution of one or more amino acids with lysine may provide additional sites for derivatization. (See U.S. Pat. No. 5,824,784 and U.S. Pat. No. 5,824,778, incorporated by reference herein).

G-CSF or derivatives thereof may be formulated for injection, or oral, nasal, pulmonary, topical, or other types of administration as one skilled in the art will recognize. The formulation may be liquid or may be solid, such as lyophilized, for reconstitution.

G-CSF or derivatives thereof are useful in the treatment of myocardial infarction or myocardial ischemia. Thus, the present methods may be useful for the treatment of such conditions. Conditions alleviated or modulated by the administration of G-CSF are typically those characterized by a reduced hematopoietic or immune function and more specifically, a reduced neutrophil count. Such conditions may be induced as a course of therapy for other purposes, such as chemotherapy or radiation therapy. Such conditions may result from infectious disease, such as bacterial, viral, fungal, or other infectious disease. For example, sepsis results from bacterial infection. Or, such condition may be hereditary or environmentally caused, such as severe chronic neutropenia or leukemias. Age may also play a factor, as in the geriatric setting; patients may have a reduced neutrophil count or reduced neutrophil mobilization. Some of such conditions are reviewed in Filgrastim (r-metHuG-CSF) In: Clinical Practice, Morstyn and Dexter (eds.), Marcel Dekker, Inc., New York (1993), p. 351. Other less-studied conditions which may be alleviated or modulated by the administration of the present analogs may include the reduction of lipids (or cholesterol) in the blood stream and certain cardiovascular conditions, as G-CSF may induce the production of plasminogen activators. In addition, the present G-CSF analog compositions may be used for mobilization of peripheral blood progenitor cells. Thus, in yet another aspect, the present invention involves a method for culturing bone marrow stem cells or peripheral blood progenitor cells with G-CSF.

In order to prepare human G-CSF containing compositions for clinical use, it will be necessary to prepare the viral expression vectors, proteins, and nucleic acids as pharmaceutical compositions,.i.e., in a form appropriate for in vivo applications. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the human G-CSF analog or an expression vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well-known in the art. Except insofar as any conventional media or agent is incompatible with the vectors or cells of the present invention, its use in therapeutic compositions is contemplated. Supplementary active ingredients also can be incorporated into the compositions.

The active compositions used in the methods of the present invention include classic pharmaceutical preparations. Administration of these compositions according to the present invention will be via any common route so long as the target tissue is available via that route. The pharmaceutical compositions may be introduced into the subject by any conventional method, e.g., by intravenous, intradermal, intramusclar, intramammary, intraperitoneal, intrathecal, retrobulbar, intrapulmonary (e.g., term release); by oral, sublingual, nasal, anal, vaginal, or transdermal delivery, or by surgical implantation at a particular site. The treatment may consist of a single dose or a plurality of doses over a period of time.

The active compounds may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents (for example, sugars or sodium chloride). Prolonged absorption of the injectable compositions can be brought about by the use in the compositions of agents delaying absorption (for example, aluminum monostearate and gelatin).

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the preferred methods of preparation are vacuum-drying and freeze-drying techniques that yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well-known in the art. Except insofar as any conventional media or agent is incompatible with the active ingredient, its use in the therapeutic compositions is contemplated. Supplementary active ingredients also can be incorporated into the compositions.

For oral administration of the compositions used in the methods of the present invention, G-CSF may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions used in the methods of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

Generally, an effective amount of G-CSF, or derivatives thereof, will be determined by the age, weight, and condition or severity of disease of the recipient. See, Remington's Pharmaceutical Sciences, supra, pages 697–773, herein incorporated by reference. Typically, a dosage of between about 0.001 µg/kg body weight/day to about 1000 µg/kg body weight/day, may be used, but more or less, as a skilled practitioner will recognize, may be used. A preferred dosage in an adult human is approximately 300 µg/day. Dosing may be one or more times daily, or less frequently, and may be in conjunction with other compositions as described herein. It should be noted that the present invention is not limited to the dosages recited herein.

"Unit dose" is defined as a discrete amount of a therapeutic composition dispersed in a suitable carrier. For example, where polypeptides are being administered parenterally, the polypeptide compositions are generally injected in doses ranging from 1 µg/kg to 100 mg/kg body weight/day, preferably at doses ranging from 0.1 mg/kg to about 50 mg/kg body weight/day. Parenteral administration may be carried out with an initial bolus followed by continuous infusion to maintain therapeutic circulating levels of drug product. Those of ordinary skill in the art will readily optimize effective dosages and administration regimens as determined by good medical practice and the clinical condition of the individual patient.

The frequency of dosing will depend on the pharmacokinetic parameters of the agents and the routes of administration. The optimal pharmaceutical formulation will be determined by one of skill in the art depending on the route of administration and the desired dosage. See, for example, Remington's Pharmaceutical Sciences, supra, pages 1435–1712, incorporated herein by reference. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein, as well as the pharmacokinetic data observed in animals or human clinical trials.

Appropriate dosages may be ascertained through the use of established assays for determining level of myocardial infarct in conjunction with relevant dose-response data. The final dosage regimen will be determined by the attending physician, considering factors that modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment.

It will be appreciated that the pharmaceutical compositions and treatment methods of the invention may be useful in fields of human medicine and veterinary medicine. Thus the subject to be treated may be a mammal, preferably a human.

In addition, the present invention contemplates a kit containing components for treating myocardial infarction comprising a composition comprising G-CSF; and optionally, at least one additional factor useful in the treatment of myocardial infarction.

F. Examples

The present invention is described in more detail with reference to the following non-limiting examples, which are offered to more fully illustrate the invention, but are not to be construed as limiting the scope thereof. The examples illustrate the treatment of an animal model of AMI with G-CSF polypeptide in vivo. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention.

EXAMPLE 1

G-CSF Administration for Repair of AMI in a Porcine Ischemia Reperfusion Model

To determine whether treatment with G-CSF polypeptide would improve cardiac function and decrease infarct-related myocardial thinning in a model of AMI and reperfusion, G-CSF was administered intramuscularly (IM) in two dosing regimens after AMI and reperfusion, one immediately after and one five days after the AMI event.

AMI was induced percutaneously in a porcine model (male Yucatan minipigs, n=19) with 90-minute proximal circumflex artery balloon occlusion followed by reperfusion. Animals were divided into 3 groups: controls (n=5); early treatment (n=5), G-CSF polypeptide (300 µg IM QOD for 20 days) beginning immediately following reperfusion; and delayed treatment, (n=9), G-CSF polypeptide (300 µg IM QD for 10 days) starting five days post AMI. All animals underwent cardiac magnetic resonance imaging (MRI) including cine-MR and contrast enhanced MR at five days (Scan 1) and 56 days (Scan 2) days post AMI. Cine-MR was performed as steady state free precession cine (true-FISP), and contrast enhanced MR was inversion recovery gradient echo (IR-FLASH). Myocardial infarct thickness was calculated as average thickness from three short axis views in the area of maximum infarction. Change in mean infarct thickness was measured as Mean infarct thickness of Scan 2 minus (−) Mean infarct thickness of Scan 1. Cardiac pathological analyses were performed at day 56. White blood cell and platelet counts were also measured to assess response to therapy.

Pigs in the early treatment group demonstrated a significant difference (P=0.01) in mean infarct thickness (−3.0±0.9) compared to controls (−4.5±0.5). No significance in mean infarct thickness was found in pigs in the delayed treatment group. No significant differences were found in percent change in overall left ventricular (LV) mass following therapy in either treatment group. Likewise, no significant differences in percent change in left ventricular ejection fraction (LVEF) were identified in either treatment group. Myocardial mass estimation by MRI was within 3% of that measured by pathology. In G-CSF-treated pigs, baseline and peak white blood cell (WBC) counts were 10±1 K/µL and 53±18 K/µL, respectively. Baseline and peak platelet counts were 536±124 K/µL and 616±144 K/µL, respectively.

Following experimental AMI with reperfusion, the immediate administration of G-CSF promoted myocardial repair by improving wall thickness in the infarct zone. However, delayed initial treatment with IM G-CSF did not improve LV remodeling or function.

EXAMPLE 2

Determining the Critical Time Period for G-CSF Administration After AMI

To determine the critical time period at which treatment with G-CSF improves cardiac function and decreases infarct-related myocardial tissue damage, G-CSF is administered in several dosing regimens after AMI but before, during, and after reperfusion therapy in a porcine model of AMI and reperfusion.

AMI is induced percutaneously in a porcine model with 90-minute proximal circumflex artery balloon occlusion followed by reperfusion. Animals are divided into multiple groups with different starting times for treatment with G-CSF (300 µg IM QOD), beginning immediately at the onset of AMI induction, and at various time intervals until 24 hours following reperfusion.

All animals undergo cardiac magnetic resonance imaging (MRI) including cine-MR and contrast enhanced MR at two time points (several to many days) post AMI. Cine-MR is performed as steady state free precession cine (true-FISP), and contrast enhanced MR is inversion recovery gradient echo (IR-FLASH). Myocardial infarct thickness is calculated as average thickness from three short axis views in the area of maximum infarction. Change in mean infarct thickness is measured as Mean infarct thickness of Scan 2 minus (−) Mean infarct thickness of Scan 1. Cardiac pathological analyses are performed. Percent in LV mass and in LVEF are also determined. Preferably LVEF is maintained or increased and there is prevention or minimization of chamber dilatation. White blood cell and platelet counts are also measured to assess response to therapy. G-CSF administration optimally elevates white blood cell count to at least $5 \times 10^9$ cells/L, but not greater than $100 \times 10^9$ cells/L, with a preferred range of $20-50 \times 10^9$ cells/L.

We claim:

1. In a reperfusion therapy method for treating acute myocardial infarction (AMI) in a mammal to reduce infarct-related myocardial tissue damage, the improvement consisting of administering an effective amount of a composition comprising Granulocyte Colony Stimulating Factor (G-CSF) polypeptide after but not before AMI, but before, concurrently with, and/or after reperfusion therapy.

2. The method of claim 1 wherein the reduction in damage is characterized by reduction in wall thickness losses.

3. The method of claim 1 wherein said reperfusion therapy consists of primary angioplasty and/or administration of a thrombolytic agent.

4. The method of claim 3 wherein said thrombolytic agent is selected from the group consisting of: streptokinase, urokinase, prourokinase, and tissue-type plasminogen activator.

5. The method of claim 1 wherein said composition comprises at least one additional factor selected from the group consisting of: EPO, SCF, M-GDF, GM-CSF, M-CSF, CSF-1, IL-1, IL-2, IL-3, IL-4, IL-5, IL-6, IL7, IL-9, IL-10, IL-11, IL-12, IGF-1, LIF, interferon, a fibroblast growth factor, and human growth hormone.

6. The method of claim 1 wherein the amount of the G-CSF polypeptide administered is 300 µg per day.

7. The method of claim 1 wherein said mammal is a human.

8. In a reperfusion therapy method for treating occlusion in an artery in a mammal to reduce tissue damage, the improvement consisting of administering an effective amount of a composition comprising Granulocyte Colony Stimulating Factor (G-CSF) polypeptide after but not before occlusion in an artery, but before, concurrently with, and/or after reperfusion therapy.

9. In a bypass surgery method for treating occlusion in an artery in a mammal to reduce tissue damage, the improvement consisting of administering an effective amount of a composition comprising Granulocyte Colony Stimulating Factor (G-CSF) polypeptide after but not before occlusion in an artery, but before, concurrently with, and/or after bypass surgery.

10. The method of claim 1 wherein the reduction in damage is characterized by an improvement in cardiac function.

11. The method of claim 1 wherein the reduction in damage is characterized by reduced scarring of the myocardium.

12. The method of claim 1 wherein the reduction in damage is characterized by reduced necrosis.

13. The method of claim 1 wherein the reduction in damage is characterized by decreased infarct-related myocardial thinning.

14. The method of claim 1 wherein the reduction in damage results in improved patient outcome.

* * * * *

UNITED STATES PATENT AND TRADEMARK OFFICE
CERTIFICATE OF CORRECTION

PATENT NO. : 7,220,407 B2  Page 1 of 1
APPLICATION NO. : 10/694579
DATED : May 22, 2007
INVENTOR(S) : Jayesh Mehta et al.

It is certified that error appears in the above-identified patent and that said Letters Patent is hereby corrected as shown below:

Title page, Item (73) correct the Assignee's name to Northwestern University, Evanston, Illinois (U.S.).

Signed and Sealed this

Eighteenth Day of September, 2007

JON W. DUDAS
*Director of the United States Patent and Trademark Office*

UNITED STATES PATENT AND TRADEMARK OFFICE
CERTIFICATE OF CORRECTION

PATENT NO. : 7,220,407 B2
APPLICATION NO. : 10/694579
DATED : May 22, 2007
INVENTOR(S) : Jayesh Mehta et al.

Page 1 of 1

It is certified that error appears in the above-identified patent and that said Letters Patent is hereby corrected as shown below:

At Column 14, line 27, "IL7" should be -- IL-7 --.

Signed and Sealed this

Twenty Second Day of April, 2008

JON W. DUDAS
*Director of the United States Patent and Trademark Office*